United States Patent
Modaressi et al.

(10) Patent No.: US 10,334,842 B1
(45) Date of Patent: *Jul. 2, 2019

(54) AGRICULTURAL ADJUVANT COMPOSITIONS, PESTICIDE COMPOSITIONS, AND METHODS FOR USING SUCH COMPOSITIONS

(71) Applicant: Solvay USA Inc., Cranbury, NJ (US)

(72) Inventors: Hedieh Modaressi, Princeton, NJ (US); Joe V. Gednalske, River Falls, WI (US); Rajesh Pazhianur, Hardley, PA (US); Andrew Douglass, East Windsor, NJ (US); Gregory K. Dahl, Eagan, MN (US)

(73) Assignee: SOLVAY USA, INC., Cranbury, NJ (US)

( * ) Notice: Subject to any disclaimer, the term of this patent is extended or adjusted under 35 U.S.C. 154(b) by 288 days.

This patent is subject to a terminal disclaimer.

(21) Appl. No.: 14/489,294

(22) Filed: Sep. 17, 2014

Related U.S. Application Data

(60) Continuation of application No. 14/489,171, filed on Sep. 17, 2014, which is a division of application No. 11/401,625, filed on Apr. 11, 2006, which is a continuation of application No. 11/227,050, filed on Sep. 15, 2005, now abandoned.

(60) Provisional application No. 60/610,051, filed on Sep. 15, 2004.

(51) Int. Cl.
| | |
|---|---|
| *A01G 22/00* | (2018.01) |
| *A01N 25/04* | (2006.01) |
| *A01N 25/30* | (2006.01) |
| *A01N 43/54* | (2006.01) |
| *A01N 57/20* | (2006.01) |

(52) U.S. Cl.
CPC ............ *A01N 25/30* (2013.01); *A01G 22/00* (2018.02); *A01N 25/04* (2013.01); *A01N 43/54* (2013.01); *A01N 57/20* (2013.01)

(58) Field of Classification Search
CPC ......... A01N 25/04; A01N 25/30; A01N 57/20
See application file for complete search history.

(56) References Cited

U.S. PATENT DOCUMENTS

| | | | |
|---|---|---|---|
| 3,506,195 A * | 4/1970 | Waldrum | ................... 239/11 |
| 5,084,087 A | 1/1992 | Hazen et al. | |
| 5,741,502 A | 4/1998 | Roberts | |
| 5,770,543 A | 6/1998 | Garst et al. | |
| 5,905,072 A | 5/1999 | Capuzzi et al. | |
| 6,068,849 A | 5/2000 | Mueninghoff et al. | |
| 6,296,864 B1 | 10/2001 | Zen | |
| 6,432,884 B1 | 8/2002 | Lachut | |
| 2003/0153462 A1 * | 8/2003 | Herold et al. | ................ 504/206 |
| 2004/0116300 A1 | 6/2004 | Schnabel et al. | |
| 2004/0192556 A1 * | 9/2004 | Schregenberger et al. | ... 504/361 |

OTHER PUBLICATIONS

Johnson et al., "Sprayer Nozzles: Selection and Calibration", University of Kentucky Cooperative Extension Service, Mar. 1996.*
Hoffmann et al. ("Evaluation of aerial spray technologies for adult mosquito control applications", Journal of Plant Protection Research, 2013, 53(3), 222-229).*
Roundup WeatherMax(R) with Transorb(R) 2 Technology MSDS from Monsanto Canada Jan. 9, 2014, p. 1-9.*
Gauvrit, Christian. "Glyphosate Response to Calcium, Ethoxylated Amine Surfactant, and Ammonium Sulfate", Weed Technology, vol. 17, Issue 4, Oct.-Dec. 2003, pp. 799-804.
Dirks et al. "Reduced rates of sulfentrazone plus chloriumuron and glyphosate in no-till, narrow-row, glyphosate-resistant Glycine max", Weed Science Technology, 48, Sep.-Oct. 2000, pp. 618-627.
Miller et al. "Johnsongrass (Sorghum halephense) Control and Rainfastness for Glyphosate and Adjuvants", Weed Technology, vol. 12, Issue 4, Oct.-Dec. 1998, pp. 617-622.
"Tips that nip drift", Mid-South Farmer, A Farm Progress Publication, Mid-South Group®, May 2000 (pp. 1-4).

* cited by examiner

*Primary Examiner* — Kortney L. Klinkel
(74) *Attorney, Agent, or Firm* — Winthrop & Weinstine, P.A.

(57) ABSTRACT

Pesticide compositions containing an adjuvant which contains, based on 100 parts by weight of the adjuvant, (a) greater than about 50 parts by weight of at least one alkyl fatty acid ester, (b) from about 2 parts by weight to less than about 5 parts by weight of a surfactant comprising: (b)(i) one or more anionic surfactants selected from sulfonic acids, sulfonic acid esters, alkylsulfosuccinic acid esters, phosphate esters, sulfate esters, and oleoyltaurate salts, or (b)(ii) one or more non-ionic surfactants selected from sorbitan fatty acid esters, aryl alkoxylates, alkoxylated fatty alcohols, alkoxylated fatty acids, alkoxylated triglycerides, alkoxy copolymers, alkylpolyglucosides, alkoxylated fatty amines, and ether amines, or (iii) a mixture (b)(i) and (b)(ii), exhibit improved performance, particularly when sprayed through a flat fan spray nozzle, an air induction spray nozzle, or other spray nozzle and at a pressure of from about 10 pounds per square inch to about 100 pounds per square inch.

26 Claims, No Drawings

AGRICULTURAL ADJUVANT COMPOSITIONS, PESTICIDE COMPOSITIONS, AND METHODS FOR USING SUCH COMPOSITIONS

CROSS REFERENCE TO RELATED APPLICATIONS

This application is a continuation-in-part of U.S. application Ser. No. 14/489,171, filed Sep. 17, 2014, which is a divisional of U.S. application Ser. No. 11/401,625, filed Apr. 11, 2006, which is a continuation of U.S. application Ser. No. 11/227,050, filed Sep. 15, 2005, which claims the benefit of U.S. Provisional Application No. 60/610,051 filed Sep. 15, 2004, the contents of each of which are hereby incorporated by reference herein in their entirety.

FIELD OF THE INVENTION

This invention relates to agricultural adjuvant compositions, pesticide compositions, and methods for using such compositions.

BACKGROUND OF THE INVENTION

Pesticide compositions, for example, herbicide compositions containing N-(phosphonomethyl)glycine ("glyphosate"), are typically applied to target plants by spraying. A portion of the spray droplets are typically very small, for example, less than about 200 microns, which are subject to off-target movement, termed "drift". Drift is undesirable because it reduces the amount of active herbicide applied to the target plant and risks unintended application of the active herbicide to non-target plants.

Common approaches to reducing drift are to add a thickening agent, for example, polysaccharides, polyacrylamides, to the herbicide composition, and/or to control process variables, such as by reducing spray pressure, or to using a spray nozzle, for example, an air induction spray nozzle, that is designed to reduce drift (note, however, that thickeners are typically not used in combination with air induction nozzles).

In addition, a wide variety of adjuvants, including adjuvant compositions that containing alkylated seed oils and emulsifiers, are generally known for use in modifying the properties, such as efficacy against target pests, of agricultural pesticide formulations, including glyphosate herbicide compositions, see, e.g., Miller, D. K., et. al., "Johnsongrass (*Sorgum halepense*) Control and Rainfastness with Glyphosate and Adjuvants", *Weed Technology*, 1998, Vol. 12:617-622, and U.S. Pat. No. 6,432,884 BI. In this example the adjuvant mainly consists of a silicone surfactant as well as alkylated seed oil and nonionic surfactants. Silicone based surfactants are known to be unstable in acidic and basic conditions. Generally the optimum pH for these surfactants is in the range of 6 to 8 (Murphy et al., Proc Brighton Crop Prot Conf—Weeds 1991). Among other disadvantages of silicone surfactants are the incompatibility with non-silicone adjuvants, reduced activity of herbicides due to spray run-offs or quick evaporation. On the other hand, some authoritative sources have discouraged use of oil adjuvants with glyphosates, e.g., North Dakota State University's 2004 North Dakota Weed control Guide states, at pg 71, that "glyphosate should never be used with oil adjuvants because glyphosate is very water soluble (water+oil do not mix)".

There remains a continuing interest in efficient spray application of pesticide compositions, particularly glyphosate compositions, to target plants with minimal drift, while maintaining high efficacy against such target plants.

SUMMARY OF THE INVENTION

In a first aspect, the present invention is directed to an adjuvant composition comprising, based on 100 parts by weight ("pbw") of the adjuvant composition:
  (a) greater than about 50 pbw of at least one alkyl fatty acid ester,
  (b) from about 2 pbw to less than about 5 pbw of a surfactant comprising:
    (i) one or more anionic surfactants selected from sulfonic acids, sulfonic acid esters, alkylsulfosuccinic acid esters, phosphate esters, sulfate esters, and oleoyltaurate salts, or
    (ii) one or more non-ionic surfactants selected from sorbitan fatty acid esters, aryl alkoxylates, alkoxylated fatty alcohols, alkoxylated fatty acids, alkoxylated triglycerides, alkoxy copolymers, alkylpolyglucosides, alkoxylated fatty amines, and ether amines, or
    (iii) a mixture (b)(i) and (b)(ii).

In a second aspect, the present invention is directed to a pesticide composition, comprising, based on 100 pbw of the pesticide composition:
  (a) from about 0.02 pbw to about 7 pbw of at least one alkyl fatty acid ester,
  (b) from about 0.001 pbw to about 0.35 pbw of a surfactant comprising:
    (i) one or more anionic surfactants selected from sulfonic acids, sulfonic acid esters, alkylsulfosuccinic acid esters, phosphate esters, sulfate esters, and oleoyltaurate salts, or
    (ii) one or more non-ionic surfactants selected from sorbitan fatty acid esters, aryl alkoxylates, alkoxylated fatty alcohols, alkoxylated fatty acids, alkoxylated triglycerides, alkoxy copolymers, alkylpolyglucosides, alkoxylated fatty amines, and ether amines, or
    (iii) a mixture (b)(i) and (b)(ii), and
  (c) an effective amount of a pesticide.

In a third aspect, the present invention is directed to a method for treating a target plant, comprising spraying onto foliage of the target plant, through a flat fan spray nozzle, an air induction spray nozzle, or other spray nozzle and at a pressure of from about 10 pounds per square inch ("psi") to about 100 psi, a pesticide composition comprising, based on 100 pbw of the pesticide composition:
  (a) from about 0.025 pbw to about 7 pbw of at least one alkyl fatty acid ester,
  (b) from about 0.001 pbw to about 0.35 pbw of a surfactant comprising:
    (i) one or more anionic surfactants selected from sulfonic acids, sulfonic acid esters, alkylsulfosuccinic acid esters, phosphate esters, sulfate esters, and oleoyltaurate salts, or
    (ii) one or more non-ionic surfactants selected from sorbitan fatty acid esters, aryl alkoxylates, alkoxylated fatty alcohols, alkoxylated fatty acids, alkoxylated triglycerides, alkoxy copolymers, alkylpolyglucosides, alkoxylated fatty amines, and ether amines or
    (iii) a mixture (b)(i) and (b)(ii), and
  (c) an effective amount of a pesticide.

The compositions and method of the present invention enable spray application of pesticide to target plants at high spray pressures by enhancing canopy penetration and hence improving deposition.

DETAILED DESCRIPTION OF INVENTION AND PREFERRED EMBODIMENTS

As used herein, the term "alkyl" means a saturated straight chain, branched chain, or cyclic hydrocarbon radical, such as for example, methyl, ethyl, n-propyl, iso-propyl, n-butyl, sec-butyl, t-butyl, pentyl, n-hexyl, cyclohexyl.

As used herein, the term "alkoxy" means a saturated straight chain or branched chain ether radical, such as for example, methoxy, ethoxy, propoxy, isopropoxy, butoxy, the term "alkoxylated" or "alkoxylate" in reference to an organic moiety means that the moiety is substituted with one or more alkoxy groups, typically with a polyether group, such as, for example a poly(ethoxy), poly(propoxy) or poly(ethoxypropoxy) group, the term "ethoxylated" in reference to an organic moiety means that the moiety is substituted with a at least one ethoxy or poly(ethoxy) group. As used herein, the notation "(n)", wherein n is an integer, in reference to the polyalkoxy group of an alkoxylated moiety indicates the number of alkoxy units in the polyalkoxy group. For example such as "ethoxylated (5) sorbitan laurate" means a sorbitan laurate alkoxylated with 5 moles of ethoxy units per mole of sorbitan laurate.

As used herein, the term "alkenyl" means an unsaturated straight chain, branched chain, or cyclic hydrocarbon radical that contains one or more carbon-carbon double bonds, such as, for example, ethenyl, 1-propenyl, 2-propenyl.

As used herein, the term "aryl" means an unsaturated hydrocarbon ring system containing one or more six-membered carbon rings in which the unsaturation may be represented by three conjugated double bonds, which may be substituted one or more of the ring carbons with hydrocarbon, typically alkyl or alkenyl, halo, or organohalo groups, such as, for example, phenyl, methylphenyl, trimethylphenyl, chlorophenyl, trichloromethylphenyl.

As used herein, the term "aralkyl" means an alkyl group substituted with one or more aryl groups, such as, for example, phenylmethyl, phenylethyl, triphenylmethyl.

As used herein, the term "aralkeny" means an alkenyl group substituted with an aryl group, such as, for example, phenylethenyl, and phenyl propenyl.

As used herein, the terminology "$(C_n$-$C_m)$" in reference to an organic group, wherein n and m are each integers, indicates that the group may contain from n carbon atoms to m carbon atoms per group.

As used herein, the terminology "fatty acids" refers to saturated or unsaturated fatty acids, typically $(C_6$-$C_{22})$ fatty acids, such as, for example, lauric acid, myristic acid, palmitic acid, stearic acid, oleic acid, linoleic acid, behenic acid, erucic acid, as well as mixtures thereof, including vegetable oils, such as, for example, rapeseed oil or canola oil, that comprise a mixture of saturated or unsaturated $(C_6$-$C_{22})$ fatty acids.

As used herein, the terminology "fatty alcohols" refers to saturated or unsaturated fatty alcohols, typically $(C_6$-$C_{22})$ fatty alcohols, such as, for example, lauryl alcohol, myristyl alcohol, stearyl alcohol, oleyl alcohol, linoleyl alcohol, behenyl alcohol, erucyl alcohol, as well as mixtures thereof.

In one embodiment, the adjuvant composition of the present invention comprises, based on 100 pbw weight of such composition, from about 50 to about 98 pbw, more typically from about 80 to about 97 pbw, of the at least one alkyl fatty acid ester.

In one embodiment, the pesticide composition of the present invention comprises, based on 100 pbw weight of such composition, from about 0.025 to about 7 pbw, more typically from about 0.05 to about 2 pbw, of the at least one alkyl fatty acid ester.

In one embodiment, the alkyl fatty acid ester comprises at least one $(C_1$-$C_6)$alkyl ester of a saturated or unsaturated $(C_6$-$C_{22})$ fatty acid, such as, for example, methyl laurate, methyl stearate, ethyl stearate, methyl oleate, ethyl oleate, butyl oleate.

In one embodiment, the adjuvant composition of the present invention comprises, based on 100 pbw weight of such composition, from about 1 to about 5, more typically from about 2 to about 4.5 pbw, and even more typically from about 2 to about 4 pbw, surfactant.

In one embodiment, the pesticide composition of the present invention comprises, based on 100 pbw weight of such composition, from about 0.001 to about 7 pbw, from about 0.025 to about 7 pbw, and even more typically from about 0.05 to about 2 pbw, surfactant.

In one embodiment, the surfactant component of adjuvant composition of the present invention comprises, based on 100 pbw weight of such composition, from about 0.1 to about 2 pbw, more typically from about 0.25 to about 1.5 pbw, and even more typically from about 0.5 to about 1.5 pbw, of the anionic surfactant, and from about 0.2 to about 4 pbw, more typically from about 0.4 to about 4 pbw, and even more typically from about 1 to about 3 pbw, of the nonionic surfactant.

In one embodiment, the surfactant component of the pesticide composition of the present invention comprises, based on 100 pbw weight of such composition, from about 0.0001 to about 1 pbw, more typically from about 0.0002 to about 0.5 pbw, of the anionic surfactant, and from about 0.0005 to about 1.5 pbw, more typically from about 0.0001 to about 1 pbw, of the nonionic surfactant.

In one embodiment, the surfactant component of the pesticide composition of the present invention comprises, based on 100 pbw weight of such composition, from about 0.01 to about 3 pbw, more typically from about 0.05 to about 1.5 pbw, of the anionic surfactant, and from about 0.01 to about 4.5 pbw, more typically from about 0.05 to about 1 pbw, of the nonionic surfactant.

Suitable sulfonic acids and sulfonic acid esters include alkyl sulfonic acids, alkylsulfonates, arylsulfonic acids, and arylsulfonates, more typically $(C_8$-$C_{30})$alkylsulfonic acids, $(C_8$-$C_{30})$alkylsulfonates, $(C_8$-$C_{30})$arylsulfonic acids, and $(C_8$-$C_{30})$aryl sulfonates, which may each be partially or completely in form of a salt, typically an alkali metal or ammonium salt. The aryl moiety of such arylsulfonic acids and arylsulfonic acid esters may optionally be substituted with one of more saturated or unsaturated hydrocarbon groups, typically $(C_4$-$C_{16})$alkyl or $(C_4$-$C_{16})$alkenyl groups. Specific examples of suitable sulfonic acids and sulfonic acid esters include xylene sulfonic acid, phenyl sulfonic acid, methane sulfonic acid, calcium dodecylbenzene sulfonate, calcium octadecylphenyl sulfonate, sodium tridecyl benzene sulfonate, isopropylamine dodecyl benzene sulfonate, isopropylamine tridecyl benzene sulfonate, ammonium tridecylphenyl sulfonate, disodium alkyldiphenyloxide sulfonate, sodium alpha olefin sulfonate, and mixtures thereof.

Suitable alkylsulfosuccinic acid esters include mono- or di-esters of alkylsulfosuccinic acids which may be may be partially or completely in form of a salt, typically an alkali metal or ammonium salt, and which may optionally, be alkoxylated, typically with up to about 100 moles of ($C_2$-$C_6$)alkoxyl units per mole of alkylsulfosuccinic acid ester. Specific examples of suitable alkylsulfosuccinic acid esters include disodium monooctylsulfosuccinate, dioctylsulfosuccinate, sodium dioctyl sulfosuccinate, disodium mono-alkylphenyl ether sulfosuccinate, disodium lauryl sulfosuccinate, disodium laureth sulfosuccinate, and mixtures thereof.

Suitable phosphate esters include mono- and di-alkyl, typically ($C_8$-$C_{30}$)alkyl, and aryl, typically ($C_8$-$C_{30}$)aryl, esters of phosphoric acid, may optionally be alkoxylated, typically with up to about 100 moles of ($C_2$-$C_6$)alkoxyl units per mole of phosphate ester, and may be partially or completely in form of a salt, typically an alkali metal or ammonium salt. The aryl moiety of such aryl phosphate esters may optionally be substituted with one of more saturated or unsaturated hydrocarbon groups, typically ($C_4$-$C_{16}$)alkyl, ($C_4$-$C_{16}$)aryl, ($C_4$-$C_{16}$)aralkenyl, or ($C_4$-$C_{16}$) aralkenyl groups. Specific examples of suitable phosphate esters include ethoxylated (8) lauryl alcohol phosphate ester, ethoxylated (9) tridecyl alcohol phosphate ester, ethoxylated (15) dinonylphenol phosphate ester, ethoxylated (6) nonylphenol phosphate ester, ethoxylated (16) tristyrylphenol phosphate ester, and mixtures thereof.

Suitable sulfate esters include alkyl sulfates and aryl sulfates, which may optionally be alkoxylated, typically with up to about 40 moles of ($C_2$-$C_6$)alkoxyl units per mole of sulfate ester, and may be partially or completely in form of a salt, typically an alkali metal or ammonium salt. The aryl moiety of such aryl sulfates may be substituted by one or more saturated or unsaturated hydrocarbon groups, typically ($C_2$-$C_{30}$)alkyl or ($C_2$-$C_{30}$)aryl groups. Suitable sulfate esters include, for example, sodium lauryl sulfate, ammonium lauryl sulfate, sodium tridecyl sulfate, and mixtures thereof.

Suitable oleoyltaurate salts include, for example, methyl oleyltaurate sodium salt.

Suitable sorbitan fatty acid esters are mono-, di-, tri-, and quaternary fatty acid, typically saturated or unsaturated ($C_6$-$C_{22}$)fatty acid, esters of sorbitan, which may be alkoxylated with from about 2 to about 100 moles ($C_2$-$C_6$)alkoxyl units per mole of sorbitan ester. Specific examples of suitable sorbitan esters include sorbitan laurate, sorbitan dilaurate, sorbitan distearate, sorbitan dioleate, sorbitan trioleate, sorbitan tetraoleate, ethoxylated (20) sorbitan laurate, propoxylated (15) sorbitan distearate, and mixtures thereof.

Suitable aryl alkoxylates include phenols, which may be substituted by one or more ($C_4$-$C_{20}$)alkyl, typically ($C_4$-$C_{12}$) alkyl, or ($C_4$-$C_{20}$)aralkyl groups that are alkoxylated with up to about 100 moles ($C_2$-$C_6$)alkoxyl units per mole of aryl alkoxylate. Specific examples of suitable aryl alkoxylates include ethoxylated mono-, di- and tri-(phenylethyl) phenols, ethoxylated (20) nonylphenol, ethoxylated (15) octylphenol, and mixtures thereof.

Suitable alkoxylated fatty acids and alkoxylated fatty alcohols, typically ($C_6$-$C_{22}$) fatty acids and alkoxylated ($C_6$-$C_{22}$) fatty alcohols, are alkoxylated with up to about 60 moles ($C_2$-$C_6$)alkoxyl units per mole fatty acid or fatty alcohol. Specific examples of suitable ($C_6$-$C_{22}$) fatty alcohols or ($C_6$-$C_{22}$) fatty acids include ethoxylated (15) tridecyl alcohol, ethoxylated (7) lauryl alcohol, ethoxylated (20) oleyl alcohol, ethoxylated (15) stearyl alcohol, and mixtures thereof.

Suitable alkoxylated triglycerides include lard, tallow, peanut oil, butter oil, cottonseed oil, linseed oil, olive oil, palm oil, grapeseed oil, fish oil, soya oil, castor oil, rapeseed oil, coprah oil, coconut oil, each alkoxylated with up to about 60 moles ($C_2$-$C_6$)alkoxyl units per mole triglyceride. Specific examples of suitable alkoxylated triglycerides include ethoxylated (30) castor oil.

Suitable alkoxy copolymers include ethoxypropoxy copolymers, such as ethoxylated polyoxypropylene, ethoxylated/propoxylated alkylphenol block co-polymers, ethoxylated/propoxylated tristyryl phenol, and mixtures thereof.

Suitable alkylpolyglucosides, include, for example, ($C_8$-$C_{14}$)alkylpolyglucosides.

Suitable alkoxylated fatty amines are alkoxylated with up to about 80 moles ($C_2$-$C_6$)alkoxyl units per mole of amine and include, for example, ethoxylated (15) tallow amine, ethoxylated (30) oleyl amine, and mixtures thereof.

Suitable ether amines include isopropyloxypropyl amine, isohexyloxypropyl amine, dodecyloxypropyl amine, tetradecyloxypropyl amine, linear alkyloxypropyl amine, and mixtures thereof.

In one embodiment, the surfactant component of the adjuvant composition of the present invention comprises a mixture of one or more alkaryl sulfonates and one or more sorbitan fatty acid esters and/or alkoxylated sorbitan fatty acid esters.

In one embodiment, the surfactant component of the pesticide composition of the present invention comprises a mixture of one or more alkaryl sulfonates and one or more sorbitan fatty acid esters and/or alkoxylated sorbitan fatty acid esters.

Suitable pesticides are biologically active compounds used to control agricultural pests and include, for example, herbicides, plant growth regulators, crop desiccants, fungicides, bacteriocides, bacteriostats, insecticides, and insect repellants.

As used herein, the terminology "effective amount" in reference to the relative amount of a pesticide in a pesticide composition means the relative amount of pesticide that is effective to control a target pest, e.g., a target plant, fungus, bacterium, or insect, when the pesticide composition is applied at a given application rate.

In one embodiment, the pesticide is glyphosate herbicide and the pesticide composition is an herbicide composition that comprises a herbicidally effective amount of glyphosate.

As used herein, the terminology "an herbicidally effective amount" in reference to the relative amount of herbicide in an herbicidal composition means the relative amount that is effective to control growth of a target plant when the herbicidal composition is spray applied to the target plant at a given application rate.

In one embodiment, the pesticide composition comprises, based on 100 pbw of the composition, from about 5 pbw to about 85 pbw, more typically from about 30 to about 70 pbw glyphosate.

The adjuvant and pesticide compositions of the present invention may each optionally further comprise one or more fatty acids.

In one embodiment, the adjuvant composition of the present invention further comprises, based on 100 pbw of such composition, up to about 10 pbw, more typically from about 0.1 pbw to about 5 pbw, of one or more fatty acids.

In one embodiment, the pesticide composition of the present invention further comprises, based on 100 pbw of such composition, up to about 7 pbw, more typically from about 0.025 pbw to about 7 pbw, of one or more fatty acids.

The adjuvant and pesticide compositions of the present invention may each, optionally, further comprise one or more agronomically acceptable solvent. Suitable solvents include, for example, water, and organic solvents, such as for example, alkylated aromatic solvents, such as toluene or alkylated naphthalenes and mineral oil fractions, such as paraffinic hydrocarbons, and alcohols, such as ethanol, propanol, butanol, isobutanol, hexanol, 2-ethylhexanol, cyclohexanol, cyclohexanol, benzyl alcohol.

In one embodiment, the adjuvant composition of the present invention further comprises, based on 100 pbw of such composition, up to about 25 pbw an organic solvent.

In one embodiment, the pesticide composition of the present invention further comprises, based on 100 pbw of such composition, up to about 10 pbw an organic solvent.

In one embodiment, the pesticide composition of the present invention is an aqueous pesticide composition that further comprises water, typically, based on 100 pbw of such composition, up to about 75 pbw water.

In one embodiment, the pesticide composition of the present invention further comprises one or more water conditioners, such as for example, chelating agents, such as ethylenediamine tetraacetic acid, complexing agents such as ammonium sulfate, and pH adjusting agents, such as citric acid and polyacrylic acid.

In one embodiment, the pesticide composition of the present invention comprises, based on 100 pbw of such composition, from about 0.02 to about 0.3 pbw, more typically from about 0.03 to about 0.2 pbw, of one or more water conditioners, typically ammonium sulfate.

The pesticide composition of the present invention may, optionally, further comprise, based on 100 pbw of the composition, up to about 1.5 pbw of other ingredients, such as one or more additional surfactants, which may include cationic surfactants, such as ethoxylated tallow amines, amphoteric surfactants, such as betaines, additional anionic surfactants, such as phosphate esters, additional nonionic surfactants, and mixtures thereof, one or more alkylpolyglycosides, one or more thickeners, such as polysaccharide thickeners, and polyacrylamide thickeners.

In one embodiment, the adjuvant composition of the present invention contains no or substantially no silicone surfactant. Typically, the adjuvant composition of the present invention does not contain any silicone surfactant.

In one embodiment, the adjuvant composition of the present invention consists essentially of, based on 100 pbw of the composition:
(a) greater than about 50 pbw of at least one alkyl fatty acid ester,
(b) from about 2 pbw to less than about 5 pbw of a surfactant comprising:
 (i) one or more anionic surfactants selected from sulfonic acids, sulfonic acid esters, alkylsulfosuccinic acid esters, phosphate esters, sulfate esters, and oleoyltaurate salts, or
 (ii) one or more non-ionic surfactants selected from sorbitan fatty acid esters, aryl alkoxylates, alkoxylated fatty alcohols, alkoxylated fatty acids, alkoxylated triglycerides, ethoxypropoxy copolymers, alkylpolyglucosides, alkoxylated fatty amines, and ether amines, or
 (iii) a mixture (b)(i) and (b)(ii), and
(c) optionally, a solvent, and, in yet another embodiment, consists solely of such ingredients.

In one embodiment, the pesticide composition of the present invention contains no or substantially no silicone surfactant. Typically, the pesticide composition of the present invention does not contain any silicone surfactant.

In one embodiment, the pesticide composition of the present invention consists essentially of, based on 100 parts pbw of the composition
(a) from about 0.02 pbw to about 7 pbw of at least one alkyl fatty acid ester,
(b) from about 0.001 pbw to about 0.35 pbw of a surfactant comprising:
 (i) one or more anionic surfactants selected from sulfonic acids, sulfonic acid esters, alkylsulfosuccinic acid esters, phosphate esters, sulfate esters, and oleoyltaurate salts, or
 (ii) one or more non-ionic surfactants selected from sorbitan fatty acid esters, aryl alkoxylates, alkoxylated fatty alcohols, alkoxylated fatty acids, alkoxylated triglycerides, ethoxypropoxy copolymers, alkylpolyglucosides, alkoxylated fatty amines, and ether amines, or
 (iii) a mixture (b)(i) and (b)(ii), and
(c) an effective amount of pesticide,
(d) water,
(e) optionally, one or more water conditioners, and
(f) optionally, up to about 25 pbw of one or more organic solvents,
and, in yet another embodiment, consists solely of such ingredients.

In one embodiment the pesticide composition is sprayed through a TEEJET™ XR 1003 (Spraying Systems, Inc.) flat fan spray nozzle at a pressure of from about 10 psi to about 90 psi, more typically from about 20 psi to about 80 psi.

In one embodiment the pesticide composition is sprayed through an air induction spray nozzle at a pressure of from about 10 psi to about 90 psi, more typically from about 20 psi to about 80 psi.

In one embodiment, the pesticide composition is spray applied to a target plant at a rate of from about 5 to about 50 gallons per acre, more typically from about 10 to about 30 gallons per acre.

Example I

The composition of Example 1 was made by mixing, based on 100 pbw of the composition, 95.2 pbw of an alkyl fatty acid ester, 1.8 pbw of a fatty acid, 0.9 pbw of a 60% solution of an anionic surfactant in 2-ethylhexanol, and 2.1 pbw of a nonionic surfactant.

Examples 2 and Comparative Examples C1-C3

The compositions of Example 1 and Comparative Examples C1-C3 were made by mixing the ingredients in the relative amount in parts by volume (pbv) listed below in TABLE I.

TABLE I

| Ex. # | Composition (pbv) |
|---|---|
| 2 | 0.86 ROUNDUP WEATHERMAX™ herbicide$_a$ + 1.25 ALLIANCE™ water conditioner$_b$ + 1 adjuvant composition of Ex. 1 |
| C1 | 0.86 ROUNDUP WEATHERMAX™ herbicide$_a$ |
| C2 | 0.86 ROUNDUP WEATHERMAX™ herbicide$_a$ + 1.25 ALLIANCE™ water conditioner$_b$ + 1 crop oil concentrate |
| C3 | 0.86 ROUNDUP WEATHERMAX™ herbicide$_a$ + 1.25 ALLIANCE™ water conditioner$_b$ + 1 methylated seed oil |

$_a$glyphosate herbicide composition available from Monsanto
$_b$ammonium sulfate water conditioner available from Agriliance LLC The compositions of Example 2 and Comparative Examples C1-C3 were each spray applied, using a XR 80015™ (Spraying Systems, Inc.) nozzle at 33 psi, to target plants, Red Root Pigweed ("RRPW"), lamb's quarter ("LQTR"), and Foxtail, at a rate of 11 ounces of ROUNDUP WEATHERMAX™ herbicide per acre and the efficacy of each of the compositions in controlling the respective target plants was evaluated. Results are set forth below in TABLE II, expressed a "% Control", calculated as untreated weed-treated weed.

TABLE II

| Ex. # | % Control at 11 oz/acre | | |
|---|---|---|---|
| | RRPW | LQTR | Foxtail |
| 2 | 88 | 87.5 | 37.5 |
| C1 | 60 | 65 | 20 |
| C2 | 70 | 70 | 22.5 |
| C3 | 72.5 | 80 | 35 |

Example 3-7 and Comparative Examples C4-C7

The compositions of Examples 3-7 and Comparative Examples C4-C6 were made by mixing the ingredients in the relative amount in parts by volume (pbv) listed below in TABLE III.

TABLE III

| Ex. # | Composition (amount per 100 gallons) |
|---|---|
| 3 | 22 oz ROUNDUP WEATHERMAX ™ herbicide$_a$ + 5 qt ALLIANCE ™ water conditioner$_b$ + 2 oz adjuvant composition of Ex. 1 |
| 4 | 22 oz ROUNDUP WEATHERMAX ™ herbicide$_a$ + 5 qt ALLIANCE ™ water conditioner$_b$ + 4 oz adjuvant composition of Ex. 1 |
| 5 | 22 oz ROUNDUP WEATHERMAX ™ herbicide$_a$ + 5 qt ALLIANCE ™ water conditioner$_b$ + 6 oz adjuvant composition of Ex. 1 |
| 6 | 22 oz ROUNDUP WEATHERMAX ™ herbicide$_a$ + 5 qt ALLIANCE ™ water conditioner$_b$ + 8 oz adjuvant composition of Ex. 1 |
| 7 | 22 oz ROUNDUP WEATHERMAX ™ herbicide$_a$ + 5 qt ALLIANCE ™ water conditioner$_b$ + 16 oz adjuvant composition of Ex. 1 |
| C4 | 22 oz ROUNDUP WEATHERMAX ™ herbicide$_a$ |
| C5 | 22 oz ROUNDUP WEATHERMAX ™ herbicide$_a$ + 5 qt ALLIANCE ™ water conditioner$_b$ |
| C6 | 22 oz ROUNDUP WEATHERMAX ™ herbicide$_a$ + 5 qt ALLIANCE ™ water conditioner$_b$ + 5.5 oz Placement ™ distillate$_c$ |
| C7 | 22 oz ROUNDUP WEATHERMAX ™ herbicide$_a$ + 2 qt adjuvant composition of Ex. 1 |

$_a$glyphosate herbicide composition available from Monsanto
$_b$ammonium sulfate water conditioner available from Agriliance LLC
$_c$petroleum distillate available from Agriliance LLC.

A particle size analysis was conducted with ROUNDUP WEATHERMAX™ herbicide in combination with several adjuvants, nozzles and pressures. Nozzles and pressures used were: AI11003™ air induction nozzle (Spraying Systems Inc.) at 40, 60 and 80 psi, TT11003 TURBO TEEJET™ nozzle (Spraying Systems Inc.) at 20, 40, 60, and 80 psi, XR11003™ Extended Range Flat Fan nozzle (Spraying Systems Inc.) at 20, 40 and 60 psi, and TF2 TURBO FLOODJET™ nozzle (Spraying Systems Inc.) at 15, 27.5 and 40 psi. Concentration of the spray volume was 10 gallons per acre ("gpa"). Droplet characteristics recorded were: 220 to 305 µm ("Dv0.1"), 421 to 562 µm ("Dv0.5"), and 620 to 853 µm ("Dv0.9") for spray nozzle pressures of 40, 60 and 80 psi. percent of volume less than 210 microns ("µm"), percent of the volume greater than 730 µm, and the range of the droplet size distribution, in µm. The unexpected aspect of this example is that the droplet size distribution is independent of the rate of the adjuvant used in the aqueous sprayable glyphosate composition.

Analysis was done using a Sympatec HELOS KF™ laser particle analyzer, equipped with an R6 lens and capable of detecting particle sizes in a range from 0.5 to 1230 microns. Each treatment was replicated three times, and replications were run consecutively. The width of the nozzle plume was analyzed by moving the nozzle across the laser by means of a linear actuator. Results are set forth in TABLES IV-VII below.

TABLE IV (Nozzle = AI11003 ™ air induction nozzle)

| Ex #. | Pressure (psi) | Dv0.1 | Dv0.5 | Dv0.9 | <210 μm | >730 μm | Range (μm) |
|---|---|---|---|---|---|---|---|
| C4 | 40 | 72 | 334 | 636 | 30.53 | 3.43 | 870 |
| | 60 | 101 | 355 | 581 | 24.33 | 0.00 | 730 |
| | 80 | 159 | 383 | 601 | 17.03 | 0.13 | 759 |
| C5 | 40 | 69 | 360 | 675 | 30.52 | 5.10 | 923 |
| | 60 | 128 | 378 | 601 | 20.28 | 0.58 | 814 |
| | 80 | 162 | 385 | 612 | 16.77 | 1.44 | 848 |
| C6 | 40 | 261 | 512 | 749 | 5.19 | 11.58 | 927 |
| | 60 | 226 | 453 | 697 | 8.07 | 6.04 | 820 |
| | 80 | 204 | 415 | 643 | 10.76 | 1.96 | 827 |
| C7 | 40 | 77 | 326 | 585 | 30.50 | 0.23 | 776 |
| | 60 | 86 | 331 | 565 | 29.22 | 0.00 | 730 |
| | 80 | 119 | 356 | 576 | 22.86 | 0.00 | 721 |
| 3 | 40 | 297 | 562 | 846 | 3.42 | 22.50 | 970 |
| | 60 | 252 | 480 | 739 | 5.83 | 9.88 | 950 |
| | 80 | 224 | 432 | 655 | 8.15 | 2.57 | 825 |
| 4 | 40 | 296 | 545 | 793 | 3.47 | 16.39 | 920 |
| | 60 | 253 | 476 | 714 | 5.73 | 7.98 | 873 |
| | 80 | 223 | 428 | 650 | 8.29 | 2.68 | 827 |
| 5 | 40 | 303 | 558 | 830 | 3.16 | 20.40 | 970 |
| | 60 | 253 | 473 | 711 | 5.78 | 7.57 | 873 |
| | 80 | 220 | 421 | 623 | 8.64 | 0.68 | 515 |
| 6 | 40 | 305 | 560 | 853 | 3.10 | 21.76 | 1103 |
| | 60 | 251 | 471 | 716 | 6.00 | 8.30 | 980 |
| | 80 | 218 | 421 | 644 | 8.90 | 2.83 | 827 |
| 7 | 40 | 304 | 555 | 815 | 3.11 | 18.91 | 970 |
| | 60 | 250 | 469 | 699 | 5.97 | 6.16 | 820 |
| | 80 | 222 | 428 | 655 | 8.48 | 3.15 | 880 |

TABLE V (Nozzle = TT11003 TURBO TEEJET ™ nozzle)

| Ex. # | Pressure (psi) | Dv0.1 | Dv0.5 | Dv0.9 | <210 μm | >730 μm | Range (μm) |
|---|---|---|---|---|---|---|---|
| C4 | 20 | 196 | 423 | 686 | 11.80 | 5.60 | 934 |
| | 40 | 134 | 329 | 594 | 24.83 | 2.37 | 844 |
| | 60 | 108 | 284 | 546 | 33.43 | 0.87 | 848 |
| | 80 | 95 | 255 | 506 | 39.57 | 0.00 | 712 |
| C5 | 20 | 191 | 413 | 671 | 12.55 | 4.49 | 934 |
| | 40 | 135 | 329 | 599 | 24.71 | 2.56 | 897 |
| | 60 | 109 | 280 | 539 | 34.00 | 0.69 | 848 |
| | 80 | 95 | 250 | 497 | 40.28 | 0.18 | 805 |
| C6 | 20 | 221 | 449 | 712 | 8.62 | 7.63 | 940 |
| | 40 | 139 | 303 | 511 | 26.15 | 0.08 | 746 |
| | 60 | 110 | 246 | 451 | 38.63 | 0.00 | 708 |
| | 80 | 94 | 213 | 406 | 49.08 | 0.00 | 592 |
| C7 | 20 | 257 | 520 | 792 | 5.82 | 15.53 | 927 |
| | 40 | 161 | 365 | 584 | 17.65 | 0.40 | 790 |
| | 60 | 125 | 309 | 545 | 27.16 | 0.61 | 799 |
| | 80 | 102 | 268 | 485 | 35.47 | 0.00 | 711 |
| 3 | 20 | 207 | 417 | 621 | 10.38 | 0.00 | 687 |
| | 40 | 136 | 295 | 496 | 27.42 | 0.00 | 699 |
| | 60 | 108 | 239 | 423 | 41.23 | 0.00 | 668 |
| | 80 | 92 | 205 | 375 | 51.70 | 0.00 | 592 |

TABLE V-continued (Nozzle = TT11003 TURBO TEEJET ™ nozzle)

| Ex. # | Pressure (psi) | Dv0.1 | Dv0.5 | Dv0.9 | <210 μm | >730 μm | Range (μm) |
|---|---|---|---|---|---|---|---|
| 4 | 20 | 205 | 414 | 632 | 10.62 | 1.67 | 780 |
|   | 40 | 131 | 282 | 477 | 30.08 | 0.00 | 699 |
|   | 60 | 103 | 227 | 410 | 44.84 | 0.00 | 588 |
|   | 80 | 89  | 194 | 354 | 55.90 | 0.00 | 527 |
| 5 | 20 | 203 | 407 | 600 | 10.89 | 0.00 | 687 |
|   | 40 | 128 | 278 | 473 | 31.08 | 0.00 | 702 |
|   | 60 | 103 | 226 | 409 | 44.96 | 0.00 | 588 |
|   | 80 | 91  | 193 | 353 | 56.39 | 0.00 | 561 |
|   | 20 | 205 | 414 | 635 | 10.57 | 2.25 | 827 |
|   | 40 | 128 | 276 | 473 | 31.37 | 0.00 | 701 |
|   | 60 | 101 | 222 | 405 | 46.11 | 0.00 | 588 |
|   | 80 | 86  | 186 | 343 | 58.73 | 0.00 | 595 |
|   | 20 | 210 | 415 | 617 | 10.02 | 0.70 | 734 |
|   | 40 | 126 | 273 | 464 | 32.05 | 0.00 | 704 |
|   | 60 | 100 | 217 | 399 | 47.64 | 0.00 | 589 |
|   | 80 | 85  | 185 | 345 | 59.31 | 0.00 | 528 |

TABLE VI (Nozzle = XR11003 ™ Extended Range Flat Fan nozzle)

| Ex. # | Pressure (psi) | Dv0.1 | Dv0.5 | Dv0.9 | <210 μm | >730 μm | Range (μm) |
|---|---|---|---|---|---|---|---|
| C4 | 20 | 116 | 311 | 529 | 27.23 | 0.00 | 717 |
|    | 40 | 65  | 192 | 363 | 55.90 | 0.00 | 562 |
|    | 60 | 55  | 168 | 315 | 64.73 | 0.00 | 530 |
| C5 | 20 | 116 | 296 | 509 | 29.29 | 0.00 | 675 |
|    | 40 | 65  | 188 | 361 | 57.05 | 0.00 | 595 |
|    | 60 | 56  | 165 | 316 | 65.99 | 0.00 | 497 |
| C6 | 20 | 133 | 275 | 456 | 30.74 | 0.00 | 621 |
|    | 40 | 102 | 215 | 370 | 48.19 | 0.00 | 588 |
|    | 60 | 90  | 195 | 337 | 56.16 | 0.00 | 525 |
| 3  | 20 | 198 | 369 | 547 | 11.82 | 0.00 | 680 |
|    | 40 | 136 | 255 | 402 | 33.08 | 0.00 | 581 |
|    | 60 | 114 | 220 | 349 | 45.77 | 0.00 | 489 |
| 4  | 20 | 198 | 370 | 554 | 11.86 | 0.00 | 682 |
|    | 40 | 139 | 260 | 404 | 31.34 | 0.00 | 481 |
|    | 60 | 115 | 222 | 350 | 45.06 | 0.00 | 524 |
| 5  | 20 | 198 | 369 | 544 | 11.97 | 0.00 | 642 |
|    | 40 | 141 | 262 | 405 | 30.85 | 0.00 | 579 |
|    | 60 | 116 | 223 | 352 | 44.61 | 0.00 | 489 |
| 6  | 20 | 195 | 367 | 547 | 12.43 | 0.00 | 682 |
|    | 40 | 141 | 265 | 413 | 30.06 | 0.00 | 582 |
|    | 60 | 116 | 225 | 354 | 43.77 | 0.00 | 492 |
| 7  | 20 | 178 | 338 | 511 | 16.36 | 0.00 | 647 |
|    | 40 | 130 | 249 | 394 | 35.38 | 0.00 | 585 |
|    | 60 | 111 | 218 | 350 | 46.89 | 0.00 | 494 |

TABLE VII (Nozzle = TURBO FLOODJET TF2 ™ nozzle)

| Ex. # | Pressure (psi) | Dv0.1 | Dv0.5 | Dv0.9 | <210 μm | >730 μm | Range (μm) |
|---|---|---|---|---|---|---|---|
| C4 | 15   | 228 | 506 | 759 | 8.10  | 12.97 | 822  |
|    | 27.5 | 164 | 454 | 809 | 15.97 | 16.27 | 999  |
|    | 40   | 136 | 413 | 759 | 20.73 | 11.83 | 1004 |
| C5 | 15   | 231 | 524 | 792 | 8.00  | 17.06 | 929  |
| e  | 27.5 | 167 | 463 | 826 | 15.43 | 17.63 | 1126 |
| I  | 40   | 142 | 421 | 786 | 19.83 | 13.52 | 1069 |
| C6 | 15   | 256 | 573 | 890 | 6.17  | 27.69 | 1058 |
|    | 27.5 | 176 | 424 | 722 | 14.74 | 8.83  | 987  |
|    | 40   | 145 | 360 | 646 | 21.61 | 4.04  | 890  |
| 3  | 15   | 228 | 521 | 818 | 8.20  | 18.85 | 980  |
|    | 27.5 | 171 | 409 | 685 | 15.77 | 5.61  | 934  |
|    | 40   | 140 | 345 | 607 | 23.28 | 2.50  | 839  |
| 4  | 15   | 218 | 505 | 823 | 9.09  | 17.99 | 980  |
|    | 27.5 | 165 | 396 | 678 | 16.91 | 5.57  | 934  |
|    | 40   | 135 | 332 | 594 | 24.97 | 2.21  | 839  |
| 5  | 15   | 216 | 493 | 790 | 9.37  | 14.97 | 980  |
|    | 27.5 | 168 | 398 | 679 | 16.41 | 5.53  | 880  |
|    | 40   | 132 | 323 | 585 | 26.35 | 1.87  | 892  |
| 6  | 15   | 215 | 491 | 777 | 9.40  | 13.93 | 980  |
|    | 27.5 | 162 | 389 | 672 | 17.65 | 5.15  | 993  |
|    | 40   | 129 | 314 | 586 | 27.82 | 2.33  | 844  |
| 7  | 15   | 227 | 514 | 820 | 8.22  | 18.33 | 980  |
|    | 27.5 | 161 | 387 | 655 | 17.79 | 3.71  | 833  |
|    | 40   | 132 | 328 | 596 | 25.95 | 2.31  | 921  |

Example 8 and Comparative Example C8

The aqueous composition of Example 8 contained, based on 5 gallons of the composition, 4 ounces AMISTAR™ fungicide (Syngenta), 4 ounces of the adjuvant composition of Example 1, 1 pint PREFERENCE™ nonionic surfactant (Agriliance LLC), and SPREADER STICKER™ nonionic surfactant.

The aqueous composition of Comparative Example C8 was directly analogous to the composition of Example 8, except that it did not contain the adjuvant of Example 1.

Plots 1-8 each contained rows of potato plants. Strips of water sensitive paper (each 1 inch by 3 inches (Spraying Systems Inc.)) were placed at four locations in each plot at each of three different heights relative to the foliage canopy, that is, above the canopy, in the middle of the canopy, and below the canopy.

The composition Comparative Example C8 was applied to Plots 1-4 and the composition of Example 8 was applied to Plots 5-8, in each case by aerial spray from an AIR TRACTOR 502™ aircraft through CP® Flat Fan Nozzles at a rate of 5 gallons per acre.

The amount of spray that reached the various locations within the foliage canopy of each of the Plots was determined by counting the number of droplet within each of 4 spots (1 cm² each) on each strip of water sensitive paper after each spray application. Results are given below in TABLE IX as (droplets/cm² paper).

TABLE IX

| Plot | Canopy | Ex. # | four counts per water sensitive paper (water droplets/cm² paper) | | | | Ave. |
|---|---|---|---|---|---|---|---|
| 1 | A | C8 | 11 | 13 | 14 | 11 | 12.25 |
| 2 | A | C8 | 12 | 6  | 2  | 6  | 6.50  |
| 3 | A | C8 | 29 | 20 | 26 | 23 | 24.50 |
| 4 | A | C8 | 25 | 16 | 24 | 28 | 23.25 |
| 1 | B | C8 | 7  | 8  | 8  | 10 | 8.25  |
| 2 | B | C8 | 14 | 6  | 10 | 6  | 9.00  |
| 3 | B | C8 | 13 | 18 | 11 | 12 | 13.50 |
| 4 | B | C8 | 8  | 10 | 11 | 3  | 8.00  |
| 1 | M | C8 | 5  | 18 | 12 | 8  | 10.75 |
| 2 | M | C8 | 9  | 5  | 3  | 3  | 5.00  |
| 3 | M | C8 | 22 | 19 | 5  | 3  | 12.25 |
| 4 | M | C8 | 20 | 21 | 15 | 24 | 20.00 |
| 5 | A | 8  | 26 | 18 | 16 | 21 | 20.25 |
| 6 | A | 8  | 22 | 17 | 15 | 25 | 19.75 |
| 7 | A | 8  | 19 | 19 | 21 | 31 | 22.50 |
| 8 | A | 8  | 25 | 30 | 32 | 23 | 27.50 |
| 5 | B | 8  | 19 | 15 | 8  | 9  | 12.75 |
| 6 | B | 8  | 10 | 14 | 22 | 21 | 16.75 |

TABLE IX-continued

| Plot | Canopy | Ex. # | four counts per water sensitive paper (water droplets/cm² paper) | | | | Ave. |
|---|---|---|---|---|---|---|---|
| 7 | B | 8 | 19 | 15 | 14 | 8 | 14.00 |
| 8 | B | 8 | 21 | 33 | 25 | 28 | 26.75 |
| 5 | M | 8 | 14 | 11 | 14 | 11 | 12.50 |
| 6 | M | 8 | 13 | 8 | 17 | 10 | 12.00 |
| 7 | M | 8 | 17 | 36 | 35 | 21 | 27.25 |
| 8 | M | 8 | 34 | 37 | 48 | 30 | 37.25 |

The overall averages and standard deviations were determined for the results given in TABLE IX and are given in TABLE X below.

TABLE X

| Ex. # | Canopy | Average | Std. Dev. |
|---|---|---|---|
| C8 | A | 16.6 | 8.5 |
| C8 | B | 9.7 | 3.6 |
| C8 | M | 12.0 | 7.7 |
| 8 | A | 22.5 | 9.0 |
| 8 | B | 17.6 | 7.3 |
| 8 | M | 22.3 | 12.4 |

The invention claimed is:

1. A method for treating a target plant with a pesticide, the method comprising:
obtaining an adjuvant composition, the adjuvant composition comprising, based on 100 parts by weight:
about 95 parts by weight of an alkyl fatty acid ester; and
about 3 parts by weight of a surfactant comprising:
about 1 part by weight of a 60% solution of at least one anionic surfactant in 2-ethylhexanol; and
about 2 parts by weight of at least one nonionic surfactant;
combining the adjuvant composition with an effective amount of a pesticide; and
spraying the combined adjuvant composition and pesticide onto the foliage of the target plant.

2. The method of claim 1, the adjuvant composition further comprising at least one additional oil.

3. The method of claim 1, wherein the combined adjuvant composition and pesticide is applied at a rate of from about 5 gallons per acre to about 50 gallons per acre.

4. A method for treating a target plant with a pesticide, the method comprising:
obtaining an adjuvant composition, the adjuvant composition comprising, based on 100 parts by weight:
about 95 parts by weight of an alkyl fatty acid ester; and
about 3 parts by weight of a surfactant comprising at least one anionic surfactant and at least one nonionic surfactant, the anionic and nonionic surfactant combined at a ratio by weight of about 0.6 to about 2;
combining the adjuvant composition with an effective amount of a pesticide; and
spraying the combined adjuvant composition and pesticide onto the foliage of the target plant.

5. The method of claim 4, the adjuvant composition further comprising at least one additional oil.

6. The method of claim 4, wherein the combined adjuvant composition and pesticide is applied at a rate of from about 5 gallons per acre to about 50 gallons per acre.

7. The method of claim 4, the adjuvant composition further comprising a fatty acid.

8. A method for treating a target plant with a pesticide composition, the method comprising:
obtaining a pesticide composition, the pesticide composition comprising:
an adjuvant composition, the adjuvant composition, comprising, based on 100 parts by weight:
about 95 parts by weight of an alkyl fatty acid ester; and
about 3 parts by weight of a surfactant comprising at least one anionic surfactant and a nonionic surfactant, wherein the surfactant comprises no more than one nonionic surfactant; and
an effective amount of a pesticide; and
spraying the pesticide composition onto the foliage of the target plant.

9. The method of claim 8, the adjuvant composition further comprising at least one additional oil.

10. The method of claim 8, wherein the pesticide composition is applied at a rate of from about 5 gallons per acre to about 50 gallons per acre.

11. The method of claim 8, the adjuvant composition further comprising a fatty acid.

12. A method for treating a target plant with a pesticide, the method comprising:
obtaining an adjuvant composition, the adjuvant composition comprising, based on 100 parts by weight:
about 95 parts by weight of an alkyl fatty acid ester; and
about 3 parts by weight of a surfactant comprising at least one anionic surfactant and at least one nonionic surfactant, wherein the surfactant does not include an alkoxylated sorbitan fatty acid ester;
combining the adjuvant composition with an effective amount of a pesticide; and
spraying the combined adjuvant composition and pesticide onto the foliage of the target plant.

13. The method of claim 12, the adjuvant composition further comprising at least one additional oil.

14. The method of claim 12, wherein the combined adjuvant composition and pesticide is applied at a rate of from about 5 gallons per acre to about 50 gallons per acre.

15. The method of claim 12, the adjuvant composition further comprising a fatty acid.

16. The method of claim 1, wherein the combined adjuvant composition and pesticide is applied at a pressure sufficient to obtain a volume of pesticide droplets smaller than 210 μm of between about 12 percent and about 47 percent of a total volume of sprayed droplets.

17. The method of claim 16, wherein the combined adjuvant composition and pesticide is applied at a pressure of 40, 60, or 80 pounds per square inch.

18. The method of claim 17, wherein the combined adjuvant composition and pesticide is applied using an extended range flat fan spray nozzle.

19. The method of claim 1, wherein:
the at least one anionic surfactant is selected from sulfonic acids, sulfonic acid esters, alkylsulfosuccinic acid esters, phosphate esters, sulfate esters, and oleoyltaurate salts; and
the at least one nonionic surfactant is selected from sorbitan fatty acid esters, aryl aloxylates, alkoxylated fatty alcohols, alkoxylated fatty acids, alkoxylated triglycerides, alkoxy copolymers, alkylpolyglucosides, alkoxylated fatty amines, and ether amines.

20. The method of claim 4, wherein the combined adjuvant composition and pesticide is applied at a pressure sufficient to obtain a volume of pesticide droplets smaller than 210 μm of between about 12 percent and about 47 percent of a total volume of sprayed pesticide droplets.

21. The method of claim 20, wherein the combined adjuvant composition and pesticide is applied at a pressure of 20, 40, or 60 pounds per square inch.

22. The method of claim 21, wherein the combined adjuvant composition and pesticide is applied using an extended range flat fan spray nozzle.

23. The method of claim 4, wherein:
the at least one anionic surfactant is selected from sulfonic acids, sulfonic acid esters, alkylsulfosuccinic acid esters, phosphate esters, sulfate esters, and oleoyltaurate salts; and
the at least one nonionic surfactant is selected from sorbitan fatty acid esters, aryl aloxylates, alkoxylated fatty alcohols, alkoxylated fatty acids, alkoxylated triglycerides, alkoxy copolymers, alkylpolyglucosides, alkoxylated fatty amines, and ether amines.

24. The method of claim 8, wherein the surfactant comprises about 1 part by weight of a 60% solution of at least one anionic surfactant in 2-ethylhexanol, and about 2 parts by weight of the nonionic surfactant.

25. The method of claim 8, wherein:
the at least one anionic surfactant is selected from sulfonic acids, sulfonic acid esters, alkylsulfosuccinic acid esters, phosphate esters, sulfate esters, and oleoyltaurate salts; and
the nonionic surfactant is selected from sorbitan fatty acid esters, aryl aloxylates, alkoxylated fatty alcohols, alkoxylated fatty acids, alkoxylated triglycerides, alkoxy copolymers, alkylpolyglucosides, alkoxylated fatty amines, and ether amines.

26. The method of claim 12, wherein the surfactant comprises about 1 part by weight of a 60% solution of at least one anionic surfactant in 2-ethylhexanol, and about 2 parts by weight of at least one nonionic surfactant.

\* \* \* \* \*